United States Patent
Musley et al.

(10) Patent No.: US 10,342,445 B2
(45) Date of Patent: Jul. 9, 2019

(54) METHOD AND APPARATUS FOR DETECTING ELECTROCARDIOGRAPHIC ABNORMALITIES BASED ON MONITORED HIGH FREQUENCY QRS POTENTIALS

(71) Applicant: Medtronic Monitoring, Inc., San Jose, CA (US)

(72) Inventors: ShaileshKumar V. Musley, Blaine, MN (US); Maneesh Shrivastav, Blaine, MN (US); Stacie Vilendrer, Santa Rosa, CA (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

(21) Appl. No.: 15/342,443

(22) Filed: Nov. 3, 2016

(65) Prior Publication Data
US 2018/0116538 A1  May 3, 2018

(51) Int. Cl.
| | | |
|---|---|---|
| A61B 5/04 | (2006.01) | |
| A61B 5/0464 | (2006.01) | |
| A61B 5/0472 | (2006.01) | |
| A61B 5/0408 | (2006.01) | |
| A61B 5/0404 | (2006.01) | |

(52) U.S. Cl.
CPC ........ *A61B 5/04014* (2013.01); *A61B 5/0464* (2013.01); *A61B 5/0472* (2013.01); *A61B 5/0404* (2013.01); *A61B 5/04085* (2013.01); *A61B 5/04087* (2013.01)

(58) Field of Classification Search
None
See application file for complete search history.

(56) References Cited

U.S. PATENT DOCUMENTS

| | | |
|---|---|---|
| 6,416,471 B1 | 7/2002 | Kumar et al. |
| 6,719,701 B2 | 4/2004 | Lade |
| 6,873,870 B2 | 3/2005 | Ferek-Petric |
| 7,233,822 B2 | 6/2007 | Hettrick et al. |
| 8,180,440 B2 | 5/2012 | McCombie et al. |
| 8,538,510 B2 | 9/2013 | Toledo et al. |
| 8,626,275 B1 | 1/2014 | Amit et al. |
| 8,688,190 B2 | 4/2014 | Libbus et al. |
| 8,706,201 B2 | 4/2014 | Beker et al. |
| 8,862,211 B2 | 10/2014 | Toledo et al. |
| 9,060,683 B2 | 6/2015 | Tran |

(Continued)

OTHER PUBLICATIONS

"Withings Wireless Blood Pressure Monitor" http://store.apple.com/us/product/HF047ZM/A/withings-wireless-blood-pressuremonitor?afid=p238|XPDdhifzdc_mtid_1870765e38482_pcrid_52243355290_&cid=aos-US-kwg-pla-btb, last viewed on Oct. 10, 2016.

(Continued)

*Primary Examiner* — Ankit D Tejani
(74) *Attorney, Agent, or Firm* — Billion & Armitage; Michael A. Collins

(57) ABSTRACT

A system and method of monitoring electrocardiogram (ECG) signals and detecting ischemic conditions. In particular, high-frequency components and low-frequency components are extracted from the monitored ECG signal. The high-frequency components are analyzed to detect reduced amplitude zones (RAZs), while the low-frequency components are utilized to detect premature ventricular contraction (PVC) beats. Potentially ischemic conditions are identified based on both RAZs and PVC beats detected.

7 Claims, 5 Drawing Sheets

(56) References Cited

U.S. PATENT DOCUMENTS

| | | | |
|---|---|---|---|
| 9,167,980 B2 | 10/2015 | Ben-David et al. | |
| 9,254,096 B2 | 2/2016 | Schultz | |
| 2003/0167012 A1 | 9/2003 | Friedman | |
| 2006/0030782 A1 | 2/2006 | Shennib | |
| 2006/0247686 A1* | 11/2006 | Girouard | A61M 5/1723 607/3 |
| 2009/0076345 A1 | 3/2009 | Manicka et al. | |
| 2010/0228103 A1 | 9/2010 | Schecter | |
| 2011/0040197 A1 | 2/2011 | Welch | |
| 2013/0035604 A1 | 2/2013 | Yu | |
| 2016/0113533 A1 | 4/2016 | Ben-David et al. | |
| 2016/0128595 A1* | 5/2016 | Fischell | A61B 5/0031 600/518 |
| 2016/0287174 A1* | 10/2016 | Joseph | A61B 5/0215 |
| 2017/0265782 A1 | 9/2017 | Vollmer | |

OTHER PUBLICATIONS

Readmissions Reducation Program. Centers for Medicare and Medicaid Services. <http://www.cms.gov/Medicare/Medicare-Fee-for-Service-Payment/AcuteInpatientPPS/Readmissions-Reduction-Program.html>.

Abboud, et al., "A spectral analysis of the high frequency QRS potentials observed during acute myocardial ischemia in dogs.", Int J Cardio.1 1990; 26, 285.

Abboud, et al., "Detection of transient myocardial ischemia by computer analysis of standard and signal-averaged high-frequency electrocardiograms in patients undergoing percutaneous transluminal coronary angioplasty.", Circulation. 1987; 76, 585.

Abboud, et al., "High frequency electrocardiography of three orthogonal leads in dogs during a coronary artery occlusion.", PACE. 1989; 12, 574.

Abboud, et al., "High frequency electrocardiography using an advanced method of signal averaging for non-invasive detection of coronary artery disease in patients with conventional electrocardiogram. ", J. Electrocardiol 1985; 19: 371-380, 371-380.

Abboud, "High-frequency electrocardiogram analysis of the entire QRS in the diagnosis and assessment of coronary artery disease.", Prog Cardiovasc Dis. 1993; 35, 311.

Abboud, et al., "The use of cross-correlation function for the alignment of ECG waveforms and rejection of extrasystoles", Comput Biomed Res. 1984; 17, 258.

Aversano, et al., "High frequency QRS electrocardiography in the detection of reperfusion following thrombolytic therapy.", Clin Cardiol. 1994; 17, 175.

Batdorf, et al., "Month-to-Month and Year-to-Year Reproducibility and High Frequency QRS ECG Signals.", Journal of Electrocardiology, vol. 37 No. 4 Oct. 2004, 289-296.

Beker, et al., "Analysis of high frequency QRS potential during exercise testing in patients with coronary artery disease and in healthy subjects.", Pacing Clin Electrophysiol. 1996; 19 (Part 1), 2040-50.

Berklap, et al., "Effects of Percutaneous Transluminal Coronary Angioplasty on Late Potentials and High Frequency Mid-QRS Potentials", Cariology 1994; 85, 216-221.

Bhargava, et al., "Myocardial infarction diminishes both low and high frequency QRS potentials: power spectrum analysis of lead II.", J Electrocardiol. 1981; 14, 57.

Conover, "Understanding Electrocardiography: Arrhythmias and the 12-lead ECG.", The C.V. Mosby Company. Fifth Edition, 1988, 323.

Franz, et al., "Localization of regional myocardial ischemia by recording of monophasic action potentials.", Circulation. 1984; 69(3), 593-604.

Goldberger, et al., "Effect of myocardial infarction on high frequency ECG.", Circulation. 1981; 64, 34.

Goldberger, et al., "Effect of myocardial infarction on the peak amplitude of high frequency QRS potentials.", Journal Electrocardiol 1980; 13, 367-372.

Hanninen, et al., "Recording locations in multichannel magnetocardiograpy and body surface potential mapping sensitive for regional exercise-induced myocardial ischemia.", Basic Res Cardiol. 2001; 96(4), 405-14.

Howie, "An evaluation of a new two electrode myocardial electrical impedance monitor for detecting myocardial ischemia.", Anesth Analg. 2001; 92(1), 12-8.

Langner, et al., "High-frequency components in the electrocardiograms of normal subjects and of patients with coronary heart disease", AM Heart J. 1961;62, 746-55.

Mason, "A new system of multiple-lead exercise electrocardiography", Am Heart J. 1966; 71, 196.

Matsushita, et al., "High-frequency QRS potentials as a marker of myocardial dysfunction after cardiac surgery.", Ann Thorac Surg 2004; 77, 1293-7.

Mehta, et al., "Sudden death in coronary artery disease: acute ischemia versus myocardial substrate", Circulation. 1997; 96, 3215-3223.

Mor-Avi, et al., "Effects of coronary occlusion on high frequency content of the epicardial electrogram and body surface electrocardiogram", Circulation . 1987; 76(1), 237-243.

Mor-Avi, et al., "Effects of coronary occlusion on high-frequency components of the epicardial electrogram and body surface electrocardiogram", Circulation . 1987; 76, 237.

Mor-Avi, "Spectral analysis of canine epicardial electrogram. Short-term variations in the frequency contect induced by myocardial ischemia.", Circ Res.1990; 66, 1681-1691.

Pahlm, et al., "Data processing of exercise ECGs", IEEE Trans Biomed Eng 1987; 34, 158.

Pettersson, et al., "Changes in high-frequency QRS components are more sensitive than ST-segment deviation for detecting acute coronary artery occlusion", J Am Coll Cardiol. 2000; 36, 1827-1834.

Pettersson, et al., "Electrocardiographic changes during prolonged coronary artery occlusion in man: Comparison of standard and high-frequency recordings", Clin Physiol. 1998; 18, 179.

Rahman, et al., "Non-invasive detection of coronary artery disease by a newly developed high-frequency QRS electrocardiogram", Physiol Meas. 2004; 25(4), 957-65.

Ringborn, et al., "The absence of high-frequency QRS changes in the presence of standard electrocardiographic QRS changes of old myocardial infarction", Am Heart J. 2001; 141, 573.

Santopietro, "The origin and characteristics of primary signal noise and interference source in the high frequency electrocardiogram", Proc IEEE. 1976; 65, 707.

Schlegel, et al., "Real-time 12-lead high-frequency QRS electrocardiography for enhanced detection of myocardial ischemia and coronary artery disease", Mayo Clin Proc. 2004;79(3), 339-50.

Sharir, et al., "Use of Electrocardiographic Depolarization Abnormalities for Detection of Stress-Induced Ischemia as Defined by Myocardial Perfusion Imaging", American Journal Cardio 2012; 109, 642-650.

Siegel, et al., "Intracardiac electrode detection of early or subendocardial ischemia", Pacing Clin Electrophysiol. 1982; 6, 892-902.

Siltanen, et al., Magnetocardiography. Chapter in MacFarlane P, eds: Comprehensive Electrocardiology vol. II. Pergamon Press, 1989, 1405-1438.

Theres, et al., "Comparison of electrocardiogram and intrathoracic electrogram signals for detection of ischemic ST segment changes during normal sinus and ventricular pace rhythms", J Cardiovasc Electrophysiol. 2002; 10, 990-995.

Tragardh, et al., "Reduced high-frequency QRS components in patients with ischemic heart disease compared to normal subjects", J Electrocardiol. 2004; 037(3): 157-62.

Van Der Ark, et al., "Genesis of high frequency notching of QRS complex in an in vivo cardiac model", Circulation. 1975; 51:257.

Zhang, et al., "QRS depolarization based intra-cardiac myocardial ischemia and infarction detection", Heart Rhythm. 2005; Supplement 2(5), Abstract # P2-87.

Zipes, et al., "Sudden cardiac death", Circulation. 1998; 98:2334-2351.

* cited by examiner

METHOD AND APPARATUS FOR DETECTING ELECTROCARDIOGRAPHIC ABNORMALITIES BASED ON MONITORED HIGH FREQUENCY QRS POTENTIALS

TECHNICAL FIELD

The present disclosure is related to medical devices, and in particular to cardiac monitoring devices.

BACKGROUND

Myocardial Ischemia is a disorder that usually is caused by a critical coronary artery obstruction, which is also known as atherosclerotic coronary artery disease (CAD). While diagnosis of myocardial ischemia prior to a heart attack is very beneficial, diagnosis is often problematic. The most conclusive diagnosis relies on imaging (e.g., nuclear myocardial scan, positron emission tomography (PET) scan, computed tomography (CT) scan, etc.) of the patient's coronary artery to visually detect obstructions. However, this is a costly and time-consuming procedure, and frequently no symptoms present themselves prior to the patient having a heart attack.

Other methods of detection involve monitoring and review of electrocardiography signals associated with the patient. Typically, these techniques monitor the electrocardiogram (ECG) signals, and in particular the characteristic shape of each cardiac cycle, which includes P, Q, R, S and T inflection points corresponding with underlying cardiac events. The presence of myocardial ischemia alters the conduction path of the depolarization wavefront, which is reflected in the monitored ECG waveform. For example, a partially blocked coronary artery may result in depression of the ST segment of the ECG waveform. A completely blocked coronary artery may result in elevation of the S-T segment of the ECG waveform. While less invasive than imaging techniques, myocardial ischemia does not always present with depressed or elevated ST segments, and therefore may fail to detect all obstructions.

It would therefore be desirable to provide a system and method of detecting electrocardiographic abnormalities indicative of myocardial ischemia that remains non-invasive.

BRIEF SUMMARY OF THE INVENTION

According to an exemplary embodiment, a method of monitoring electrocardiogram (ECG) signals and detecting ischemic conditions includes extracting high-frequency components and low-frequency components from the monitored ECG signal. The high-frequency components are analyzed to detect reduced amplitude zones (RAZs), while the low-frequency components are utilized to detect premature ventricular contraction (PVC) beats. Potentially ischemic conditions are identified based on both RAZs and PVC beats detected.

According to another exemplary embodiment, a method of localizing detected ischemia includes monitoring electrocardiogram (ECG) signals from a plurality of electrodes to generate a plurality of ECG sensing vectors. High-frequency components associated with each of the plurality of ECG sensing vectors are extracted and utilized to detect reduced amplitude zones (RAZs). A potentially ischemic condition is detected based, in part, on the presence of detected RAZs in one or more of the sensing vectors. A location estimate is generated for the detected ischemic condition based on the sensing vectors utilized to detect the RAZs.

According to another exemplary embodiment, a system for monitoring electrocardiogram (ECG) signals and detecting potential ischemic conditions includes a first medical device and a processing module. The first medical device comprises one or more electrodes and sensing circuitry for monitoring ECG signals associated with a patient. The processing module is configured to receive the monitored ECG, wherein the processing module includes filtering circuitry to extract high-frequency components and low-frequency components from the monitored ECG. The processing module analyzes the high frequency components to detect reduced amplitude zones (RAZs) and analyzes the low-frequency components to detect premature ventricular contractions (PVCs). Based on the detected RAZs and PVCs, the processing module detects potential ischemic conditions.

DETAILED DESCRIPTION

The present invention relates generally to monitoring and detection of electrocardiographic abnormalities based on high-frequency (HF) components and low-frequency (LF) components of the monitored electrocardiogram (ECG) signal. In one embodiment, a portion of the HF component corresponding with a monitored QRS complex—referred to herein as the HFQRS—is analyzed by extracting a HF QRS envelope. The HFQRS envelope is analyzed to detect reduced amplitude zones (RAZ), the presence of which indicates a bimodal peak in the low-frequency envelope. Detection of a RAZ may be quantified using a number of techniques, such as peak-to-peak measurements, root-mean-square (RMS) of the low-frequency envelope, as well as via other techniques. In addition to analysis of HFQRS, an embodiment of the present invention monitors LF components to detect cardiac abnormalities. In one embodiment, analysis of the LF components includes detection of premature ventricular contractions (PVCs). The detection of bimodal peaks in the HF QRS signal is utilized in conjunction with the detection of PVC beats to determine whether the monitored ECG signal is indicative of an ischemic condition. If the combination of bimodal peaks detected in the HF QRS signal and detected PVC beats indicates a potential ischemic condition, the monitored ECG signal (including one or both of the HF components and LF components) are provided to a remote monitoring center for review.

Figure 1:
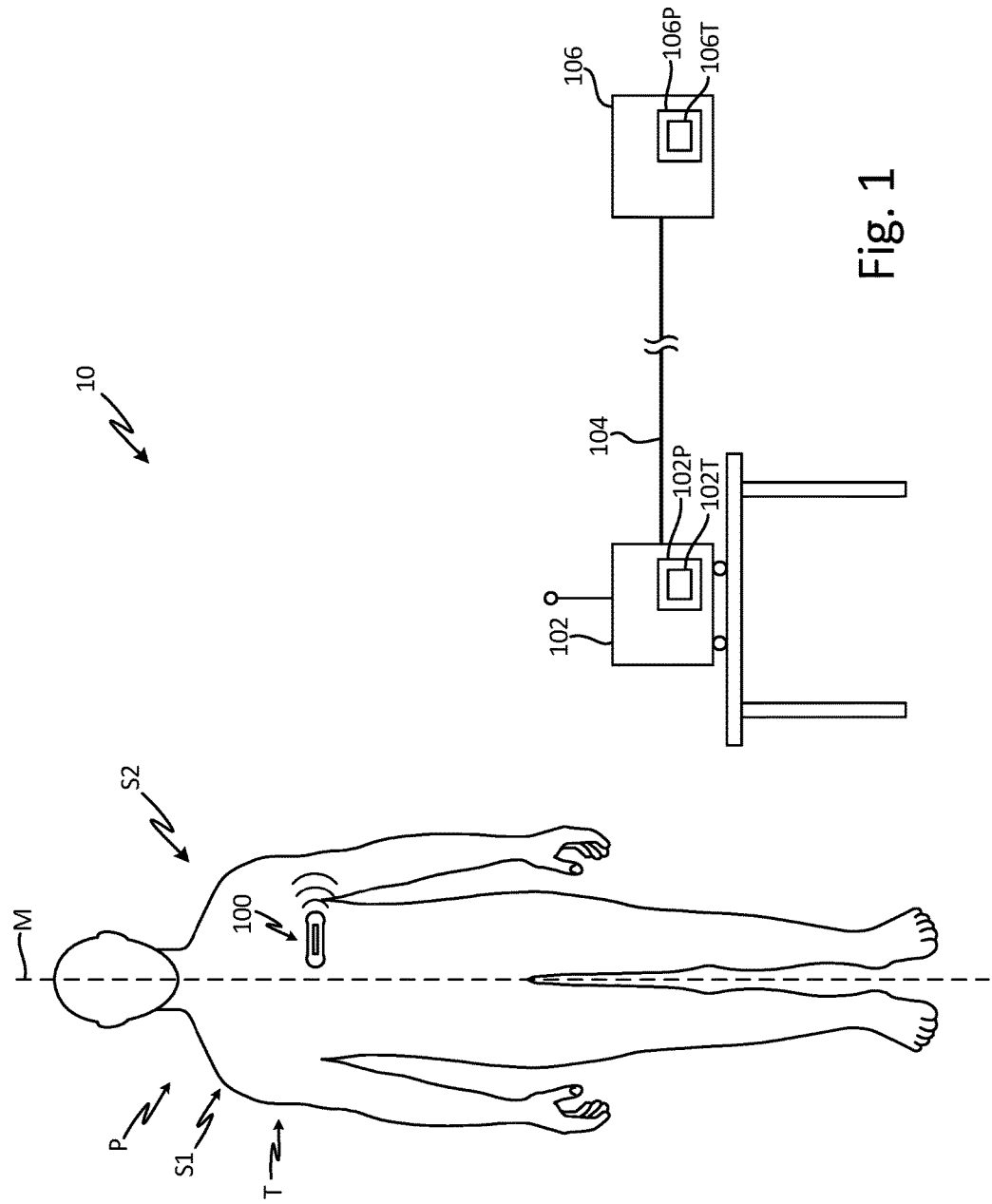
FIG. 1 is a schematic view of a patient and a patient monitoring system, according to one or more embodiments of the present invention.

FIG. 1 is a schematic view of a patient and a patient monitoring system, according to one or more embodiments of the present invention. FIG. 1 illustrates a patient P and a monitoring system 10, according to one or more embodiments of the present disclosure for monitoring cardiac activity. Patient P comprises a midline M, a first side S1, for example a right side, and a second side S2, for example a left side. Monitoring system 10 comprises a patient medical device 100, gateway 102, and remote monitoring center 106. In the embodiment shown in FIG. 1, patient medical device 100 is an adherent device that attaches to the skin of the patient, but in other embodiments may be an implantable device, an insertable device, an injectable device, or a wearable device such as a Holter monitor (collectively referred to as a medical device). Exemplary embodiments of suitable medical devices are described in more detail with respect to FIGS. 5 and 6, below. In general, medical device 100 is described herein as providing a monitoring function, but in other embodiments may be configured to provide treatment as well.

Medical device 100 can be adhered/injected/inserted to a patient P at many locations, for example thorax T of patient P. In many embodiments, the device may adhere to one side of the patient, from which side data can be collected. A benefit of utilizing an adherent device, implantable, or injectable device is that it may be utilized to collect physiological data from the patient while the patient goes about normal day-to-day activities outside of a hospital setting (i.e., ambulatory monitoring). Medical device 100 may monitor a number of physiological parameters associated with patient P, including electrocardiogram (ECG) signals utilized to detect rhythm abnormalities as well as activity level data, posture, bio-impedance, etc. Analysis of the ECG signals to detect electrocardiographic abnormalities may be done locally by medical device 100 or remotely by gateway 102 and/or remote monitoring center 106 (or similar platform separate from medical device 100).

As discussed in more detail below, analysis of the ECG signals include monitoring both low-frequency components and high-frequency components of the ECG signal. In one embodiment, the low-frequency component operates in a range less than 150 Hertz (Hz). In another embodiment, the low-frequency component are selected/filtered in the range of 0-40 Hz. In general, the low-frequency components are utilized to monitor ECG waveform components such as the P-wave, T-wave and QRS complex depolarizations. In one embodiment, the low-frequency components are utilized to detect cardiac abnormalities such as premature ventricular contractions (PVC) and arrhythmic conditions such as tachycardia and/or bradycardia. In one embodiment, the high-frequency components are selected/filtered in the range of 150-250 Hz. In other embodiments, the high-frequency component operates in a range greater than 150 Hz. The monitored high-frequency component associated with the QRS complex—referred to herein as the High-Frequency (HF) QRS—is extracted and analyzed to detect the presence of reduced amplitude zones which are indicative bimodal peaks in the HF QRS signal. Filtering and analysis of the HF QRS signal is in addition to monitoring of low-frequency components typically utilized in cardiac monitoring—including monitoring of P-waves, QRS complexes, and T-waves. Analysis of the low-frequency components are utilized to detect rhythm abnormalities, such as arrhythmias and other conditions such as premature ventricular contractions (PVCs).

In embodiments in which the ECG signals are analyzed locally by medical device 100, a filter circuit (not shown) is utilized to identify high-frequency components within the monitored ECG signal. In one embodiment, the filter circuit is a band-pass filter that isolates ECG frequencies in the range of 150 Hertz (Hz) to 250 Hz. In other embodiments, the high-frequency components may be comprised of other frequency ranges. In addition to monitoring high-frequency components (e.g., 150-250 Hz), medical device 100 may also monitor ECG signals in a lower-frequency range (e.g., 0-150 Hz, although typically 0-40 Hz). The low-frequency range is utilized to detect typical morphological structures utilized in cardiac monitoring, such as P-waves, QRS complexes, and T-waves. In particular, the low-frequency component of the monitored ECG signal can be utilized to detect rate-based arrhythmias as well as other type of arrhythmias such as premature ventricular contractions (PVCs). In response to a detected rhythm abnormality, medical device 100 captures/stores an ECG segment corresponding with the detected abnormality. The captured ECG segment is subsequently transmitted to remote monitoring center 106 for review by a health care professional (HCP). Communication of the captured ECG segment may be immediate, or may be delayed for a period of time (i.e., until it is possible/cost effective to communicate the stored ECG segment). In response to the received ECG samples, the expert/physician may verify the detected rhythm abnormality and take appropriate steps (e.g., prescribe treatment).

In other embodiments in which ECG signals are not analyzed by medical device 100 locally, monitored ECG signals are communicated wirelessly to an external processor such as gateway 102 or remote monitoring center 106 for analysis and detection of potential ischemic conditions. As discussed above, gateway 102 and/or remote monitoring center 106 utilizes high-frequency components as well as low-frequency components to detect ischemic events. In response to a detection of events indicating ischemia, monitored ECG signals—including one or more of monitored high-frequency components and low-frequency components—are stored for subsequent review by a HCP to verify the indication of potential ischemia. This may include a review of the monitored high-frequency components and low-frequency components, but may also include additional tests such as imaging of the patients arteries for obstructions.

In the embodiment shown in FIG. 1, medical device 100 communicates wirelessly with remote center 106. The communication may occur directly (via a cellular or Wi-Fi network), or indirectly through intermediate device or gateway 102. As described above, in one embodiment ECG signals monitored by medical device 100 are communicated in their entirety to remote center 106 for analysis. In other embodiments, medical device 100 processes the monitored ECG signals locally using high-frequency components and low-frequency components to detect potential ischemic conditions.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by HCPs to verify accuracy. Reports may then be generated at remote monitoring center 106 for communication to the patient's physician or care provider. In one embodiment, in addition to one-way communication from medical device 100 to gateway 102 and/or remote monitoring center 106, remote monitoring center 106 may communicate/push information to medical device 100, either to program/initialize medical device 100 or update the values stored by medical device 100.

In an exemplary embodiment, monitoring system 10 comprises a distributed processor system with at least one processing module (not shown) included as part of medical device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T (e.g., electronic, magnetic and optical storage media). Remote processor 106P may comprise a backend server located at the remote center. Physiological parameters—including ECG samples—monitored by medical device 100 may be analyzed by one or more of the distributed processors included as part of medical device 100, gateway 102, and/or remote monitoring center 106.

Figure 2:
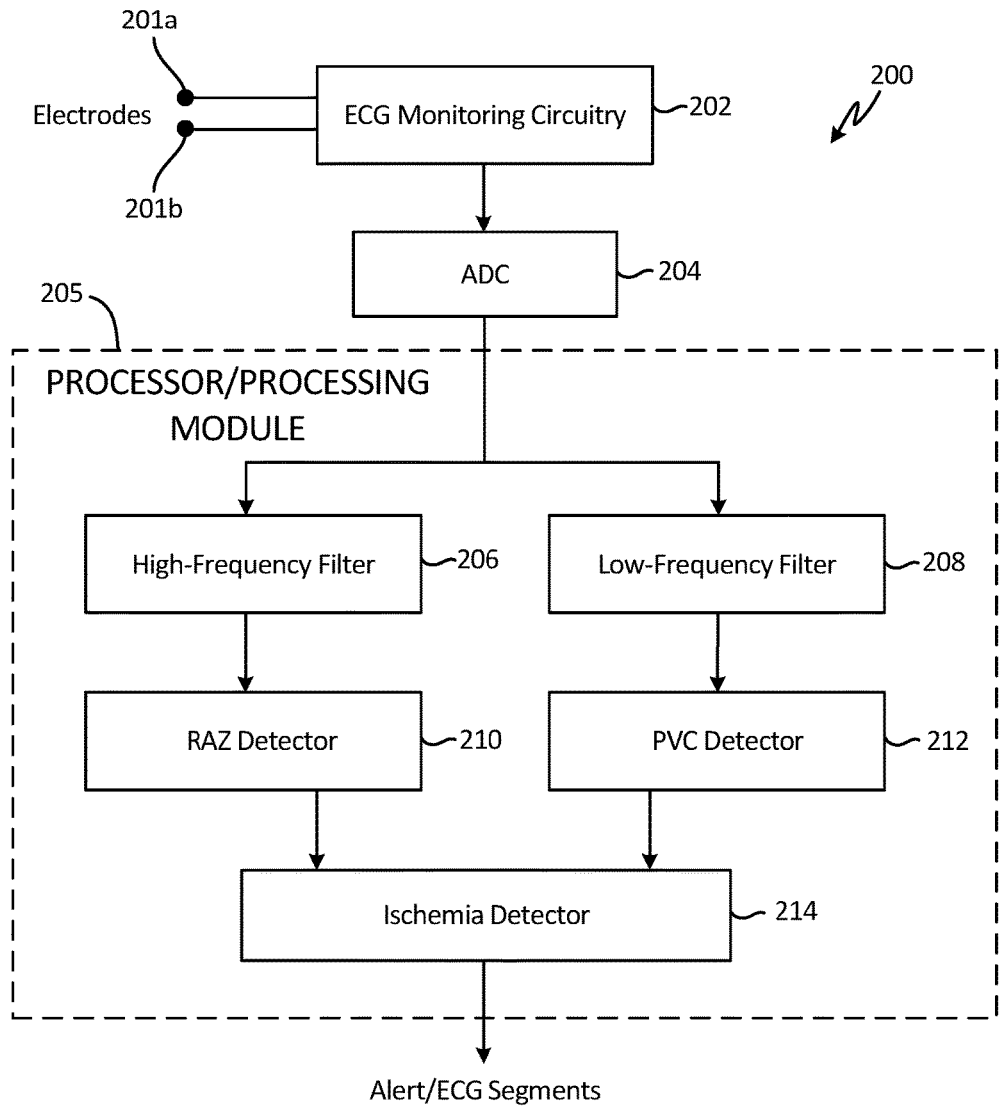
FIG. 2 is a block diagram that illustrates a system utilized to detect ischemia according to an embodiment of the present invention.

FIG. 2 is a block diagram that illustrates system 200 utilized to detect ischemia according to an embodiment of the present invention. In the embodiment shown in FIG. 2, system 200 includes electrodes 201*a*, 201*b*, ECG monitoring circuitry 202, analog-to-digital converter 204, and processor or processing module 205, which includes high-frequency filter 206, low-frequency filter 208, reduced amplitude zone (RAZ) detector 210, PVC detector 212, and ischemia detector 214.

As discussed above with respect to FIG. 1, medical device 100, gateway 102, and remote center 106 all include processors in communication with other processors to allow for implementation of one or more of the components shown in FIG. 2. In one embodiment, the components illustrated in FIG. 2 are implemented on medical device 100 to detect in real-time potential ischemic conditions and communicate monitored ECG signals representative of detected ischemic conditions to monitoring center 106 for review and subsequent action. However, it should be understood that in other embodiments, these components may be implemented remotely from medical device 100.

Electrodes 201*a* and 201*b* are implanted, affixed, adhered, or otherwise in contact with tissue of the patient to allow for monitoring of electrical signals by ECG monitoring circuitry 202. In this embodiment two electrodes are shown, but in other embodiments a plurality of electrodes may be utilized, each providing a unique sensing vector.

ECG monitoring circuitry 202 monitors the electrical signals received at electrodes 201*a* and 201*b* and provides the analog signal to analog-to-digital converter (ADC) 204 for conversion to a digital ECG signal. Because subsequent steps rely on high-frequency content extracted from the monitored ECG signal, sampling of the analog signal for generation of the digitized ECG signal utilizes a sufficiently high sampling rate (e.g., 1K Hz) to preserve the fidelity of the monitored ECG signal. In one embodiment, ADC converter 204 utilizes a 12-bit digital output, at a sampling frequency of 1K Hz.

The digitized (high-fidelity) ECG signal is processed by components 206-214 to detect potentially ischemic conditions. In the embodiment shown in FIG. 2, digitized ECG signals are processed by processor/processing module 205, wherein the processor (e.g., local processor included on medical device 100, gateway 102 or remote center 106) implements functionality illustrated by components 206-214, including filtering and processing of filtered signals. Thus, in the embodiment shown in FIG. 2, the digitized ECG signal is provided to high-frequency filter 206 and low-frequency filter 208 for filtering. High-frequency filter 206 extracts high-frequency components from the monitored ECG signal (e.g., within the range of 150-250 Hz), while low-frequency filter 208 extracts low-frequency components from the monitored ECG signal (e.g., within the range of 0-40 Hz). In other embodiments, however, components 206-214 may be implemented by discrete components.

High-frequency components are provided to reduced amplitude zone (RAZ) detector 210, which processes high-frequency components associated with QRS complexes (referred to herein as HF QRS) and detects morphological characteristics associated therewith. In particular, a normal HF QRS signal is comprised of a plurality of local maximums and local minimums, wherein a line drawn that connects local maximums and another line drawn that connects local minimums results in an HF QRS envelope that is defined by a single peak. An abnormal HF QRS signal—one indicative or potential ischemia—is defined by an HF QRS envelope that includes a reduced amplitude zone flanked by bimodal peaks. RAZ detector 210 is capable of detecting and/or quantifying the detected RAZ. Quantifying may include measuring a depth (e.g., peak-to-trough) of the RAZ, an area of the RAZ, and/or a root mean square (RMS) value of the HF QRS envelope.

In one embodiment, RAZ detector 210 analyzes each received HF QRS complex for RAZs or bimodal peaks. In other embodiments, RAZ detector 210 may utilize QRS averaging of a plurality of HF QRS complexes (e.g., 20 to 30), wherein the averaged HF QRS signal is utilized to detect RAZs or bimodal peaks.

In addition to monitoring and analyzing high-frequency components, low-frequency filter 208 and PVC detector 212 operate to detect PVC events. As discussed above, low-frequency filter 208 filters the digitized ECG signal to isolate low-frequency components (e.g., in the range of 0-40 Hz). Low-frequency components correspond with typical morphological structures utilized in cardiac monitoring, including P-waves, QRS complexes, and T-wave. In the embodiment shown in FIG. 2, low-frequency components are provided to PVC detector 212 to detect the presence of PVC beats. A number of methods may be utilized to identify and differentiate typical QRS complexes from PVC beats. For example, morphological differences such as amplitude and width of the QRS complex may be utilized to distinguish between QRS complexes and PVC beat—wherein PVC beats are characterized by higher-than-usual peak amplitudes and wide QRS complexes. The clinical significance of detected PVC beats is related to the frequency and/or complexity of the detected PVC beats. As a result, both detected PVC beats and/or a count of detected PVC beats may be provided to ischemia detector 214.

Ischemia detector 214 receives as inputs the RAZ detects (i.e., bimodal peak detects) generated by RAZ detector 210 and PVC density/frequency detected by PVC detector 212. Based on a fusion of the received inputs, ischemia detector 214 determines whether an ischemic condition is likely and generates an alert in response. In one embodiment, RAZ detector 210 provides a count of detected RAZ events (i.e., HF QRS complexes defined by bimodal peaks), while PVC detector 212 provides a count of detected PVC beats indicative of the density and/or frequency of detected PVC beats.

The respective counts are compared to threshold values by ischemia detector 214, and if both counts exceed threshold values, then ischemia detector 214 generates an alert indicating a potential ischemic event. In other embodiment, other means of fusing the output of RAZ detector 210 and PVC detector 212 may be utilized to detect ischemic events.

Figure 3:
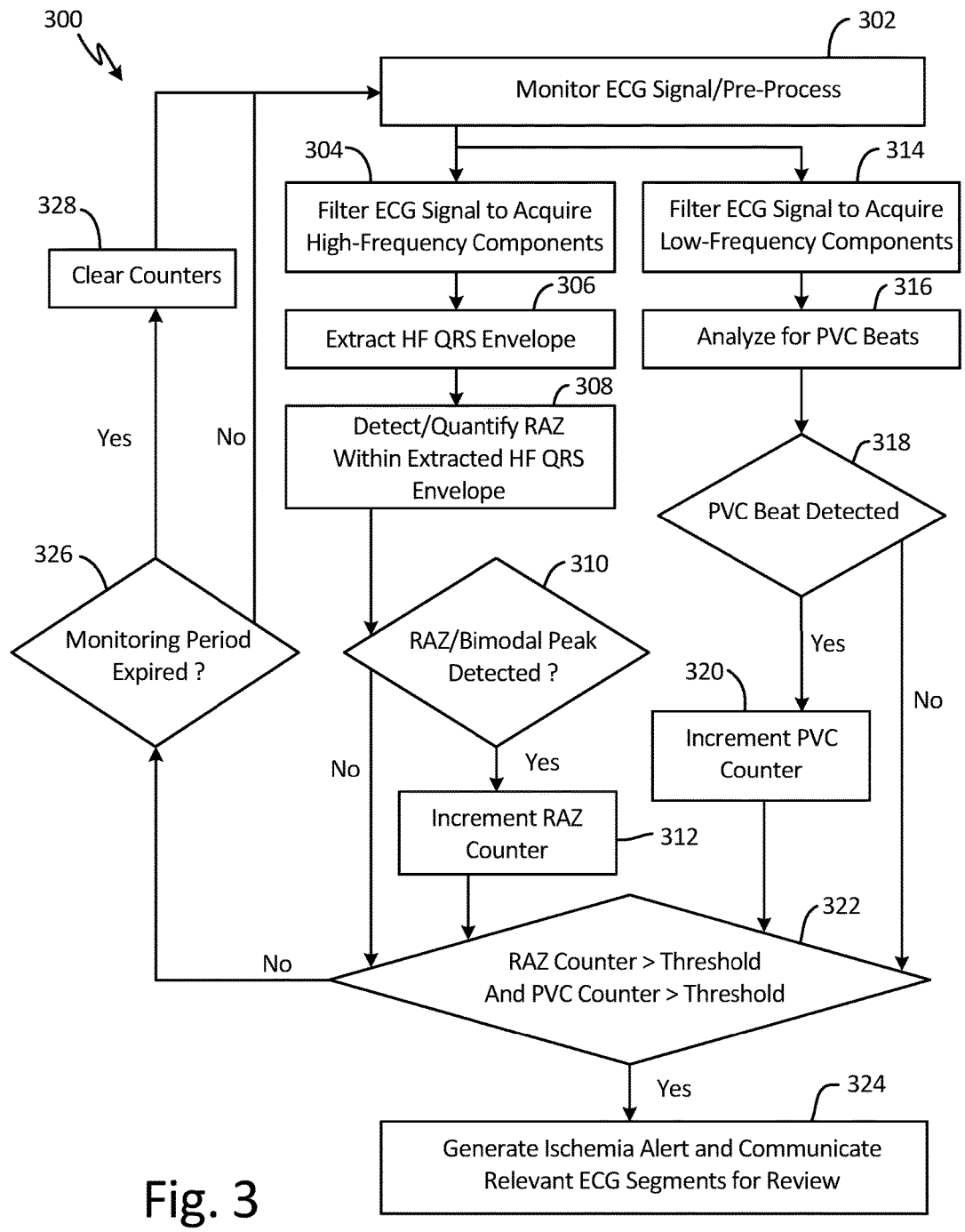
FIG. 3 is a flowchart of a method of detecting ischemia based on extraction of high-frequency QRS signals according to an embodiment of the present invention.

FIG. 3 is a flowchart of a method of detecting ischemia based on extraction of high-frequency QRS signals according to an embodiment of the present invention. At step 302, the ECG signal is monitored by medical device 100. In one embodiment, a wide band ECG is monitored to allow subsequent filtering of the ECG signal into high frequency components and low frequency components. In addition, monitoring of the ECG signal at 202 may include conditioning the monitored ECG signal for subsequent analysis. For example, in one embodiment the wide band ECG signal is passed through an anti-aliasing filter and then digitized by an analog-to-digital converter (ADC) with a relatively high sampling rate (e.g., 1K Hz).

At steps 304 and 314 the wide band ECG signal is filtered into high-frequency components and low-frequency components, respectively. In one embodiment, high frequency components are monitored within a frequency range of approximately 150 Hz to 250 Hz. Conversely, low frequency components are monitored within a frequency range of approximately less than 150 Hz, and generally less than 100 Hz. In one embodiment, filtering of high frequency components is focused on the portion of the ECG signal associated with the QRS complex. Thus, in some embodiments, high-frequency filtering includes identification of QRS complexes and corresponding filtering of these complexes, wherein the resulting high-frequency component may be referred to as the high-frequency QRS (HF QRS) signal. In other embodiments, however, high-frequency filtering is applied to the entire ECG signal.

In addition, in one embodiment high-frequency filtering provided at step 304 includes averaging the monitored ECG signals corresponding with a plurality of beats (e.g., QRS complexes) to reduce the relative contribution of uncorrelated noise. For example, in one embodiment, a plurality of QRS complexes are identified and aligned with one another to generate an average QRS signal. The number of QRS complexes included in the average may be selected based on various circumstances (e.g., type of medical device utilized to monitor), but in one embodiment may include 20-30 QRS complexes averaged together with the use of a cross-correlation function to reduce the relative contribution of noise. In addition, in one embodiment averaging QRS complexes may include excluding non-QRS complexes (i.e., extrasystoles). Typically, extrasystoles such as premature ventricular contractions (PVC) beats contain different high-frequency information than QRS complexes. For example, PVC beats may not include bimodal peaks, and therefore will introduce unwanted artifacts if included in the averaged QRS signal. However, as discussed in more detail with respect to steps 314, 316, 318, and 320 detection of PVC beats is utilized as an additional factor in the detection of ischemia. In this way, high-frequency filtering at step 304 provides as an output a HFQRS signal illustrated in FIG. 3.

At step 306, an HFQRS envelope is extracted from the high-frequency components. In general, extraction of the HFQRS envelope involves drawing a line that connects local maxima and local minima to outline the morphological shape of the HFQRS envelope, wherein the local maxima reflect the top portion of the envelope and the local minima reflect the bottom portion of the envelope.

At step 308, the HFQRS envelope is analyzed to detect/quantify a reduced amplitude zone (RAZ), which as the name implies refers to a portion of the HFQRS envelope that has a reduced amplitude. Morphologically, this presents itself as bimodal peaks separated by the area of reduced amplitude between each peak. The presence of a RAZ may be detected/quantified in several different ways. For example, the HFQRS envelope may be analyzed and a RAZ detected when at least two local maxima of the signal's upper envelope or two local minima of the signal's lower envelope are present, wherein local maximum or minimum of the HFQRS envelope is defined as an HF sample point (peak or trough) within the QRS interval wherein the absolute value of its voltage exceeds that of the three envelope sample points (peaks or troughs) immediately preceding and following it. In other embodiments, RAZ is quantified by measuring the depth of the RAZ (i.e., amplitude difference between one of the local maxima or minima and the RAZ amplitude), and/or the area of the RAZ (i.e., incorporating depth and width of the RAZ). Quantification of the RAZ allows thresholds to be utilized to determine whether the RAZ is clinically significant, versus detection of whether a RAZ is present or not. In still other embodiments, the presence of a RAZ can be quantified through root mean square (RMS) averaging of the HFQRS envelope, wherein the presence of a RAZ is indicated based on a reduction in the RMS value of the HFQRS envelope as compared with earlier measured RMS values of the HFQRS envelope.

At step 310, the detected/quantified RAZ is utilized to determine whether the HFQRS signal includes bimodal peaks characteristic of a possible ischemic condition. In embodiments in which the RAZ is quantified at step 308, then bimodal peak detection at step 310 may include comparison of the quantified RAZ value to a threshold value, wherein the presence of bimodal peaks is detected only if the quantified RAZ value exceeds the threshold. In other embodiments, the detection of bimodal peaks is a binary determination (bimodal peaks are either present or not present). If a bimodal peak is detected at step 310, then at step 312 a RAZ counter is incremented indicating the detected bimodal peak, and the incremented counter is utilized in conjunction with other monitored features to determine whether an ischemic condition is present at step 322. If no bimodal peak is detected at step 310, then the RAZ counter is not incremented (i.e., step 312 is skipped) and the method continues at step 322 to detect whether an ischemic condition is present.

Returning to step 314, while high-frequency components are monitored and analyzed for the detection of bimodal peaks, low frequency components are filtered and analyzed to detect PVC beats. In particular, at step 314 the monitored ECG signal is filtered to acquire low-frequency components. As discussed above, low frequency components are monitored within a frequency range of approximately less than 150 Hz, and generally less than 100 Hz.

At step 316, the low-frequency components are analyzed to detect the presence of PVC beats. A variety of methods are available to identify and detect PVC beats in a monitored ECG signal. In some embodiments, the amplitude/morphology of beats are analyzed and characteristics of PVC beats—such as increased amplitude or wide QRS complex—are utilized to determine whether a beat is a PVC beat. In other embodiments, either alone or in combination with utilizing amplitude/morphology, utilizes the R-R interval to determine the likelihood of a PVC beat.

In contrast with analysis of HF QRS analysis, in which at least in some embodiments a plurality of QRS complexes are averaged together, low-frequency analysis to detect PVC beats operates on a beat by beat basis to detect abnormal, PVC beats.

At step 318, a determination is made whether a PVC beat has been detected. If a PVC beat is detected at step 318, then at step 320 a PVC beat counter is incremented indicating the detected PVC beat. In some embodiments, the clinical relevance of detected PVC beats includes the frequency and/or density of detected PVC beats. In this embodiment, a counter is utilized to capture PVC density/frequency attributes, but in other embodiments other means of quantizing the frequency/density of PVC beats may be utilized. In the embodiment shown in FIG. 3, the incremented counter is utilized in conjunction with the RAZ counter to determine whether an ischemic condition is present at step 322. If no PVC beat is detected at step 318, then the PVC beat counter is not incremented (i.e., this step is skipped) and the method continues at step 322 to detect whether an ischemic condition is present.

At step 322, the bimodal peak counter and the PVC counter are compared to respective threshold values. If both the bimodal peak counter and the PVC counter exceed their respective threshold values, this indicates a possible ischemic condition. If one or both of the bimodal peak counter and PVC counter fail to exceed the threshold values, then no alerts are generated regarding a possible ischemic condition. In other embodiments, other methods of fusing information associated with detected bimodal peaks and detected PVCs may be utilized instead of comparison to threshold values. For example, in one embodiment a combination or sum of the detected bimodal peaks may be combined with number of detected PVC beats to detect ischemia. If the bimodal peak counter and PVC counter both exceed the respective thresholds (or, similarly, if the fusion of the counter values exceeds a threshold value) then at step 324 a determination is made that the monitored ECG period is indicative of a possible ischemic condition. In one embodiment, in response to a determination of a potentially ischemic condition results in ECG segments corresponding with the detected ischemic condition are communicated to a remote monitoring center for review. That review may include additional review by a health care professional (HCP) of the monitored ECG signals to verify the detected ischemic condition. In some embodiments, the HCP may utilize or tests/analysis to verify the condition. For example, in one embodiment, the HCP reviews the amplitude of the S-T segment to verify the detected ischemia. In other embodiments, the HCP may request imaging of the patient to verify the ischemic condition.

If at step 322 one or more of the bimodal peak counter and/or PVC counter does not exceed the threshold values, then at step 326 a determination is made whether the monitoring period has expired. If the monitoring period has not expired, then the values of the counters are preserved and monitoring of the ECG signal continues at step 302. If the monitoring period has expired, then both of the respective counters are cleared or reset at step 328, and monitoring continues at step 302.

In this way, the method utilizes a combination of HF QRS analysis and PVC detection to detect ischemic conditions. In response to a detected ischemic condition, monitored ECG segments representative of the detected ischemic condition are communicated to a remote monitoring center for review and verification. This may include review of the HFQRS and PVC analysis, and may further include review of other factors (such as ST segment morphology, or imaging analysis) to verify the detected ischemic condition.

Figure 4A:
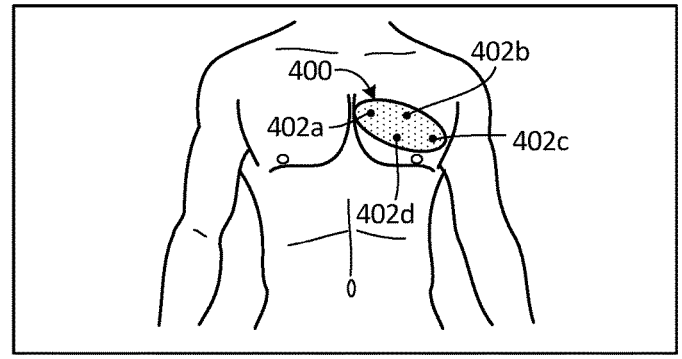
FIGS. 4a-4c are schematic views illustrating location of electrode placement according to an embodiment of the present invention.
Figure 4B:
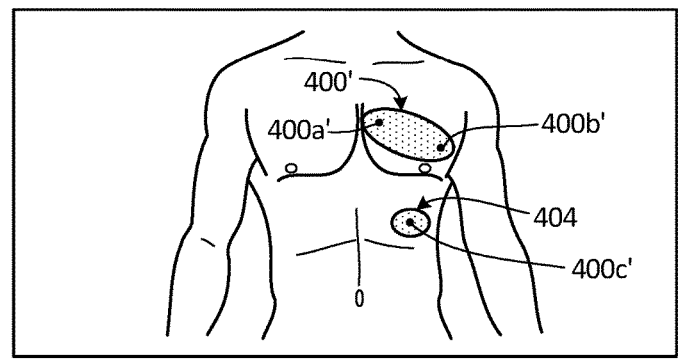
Figure 4C:
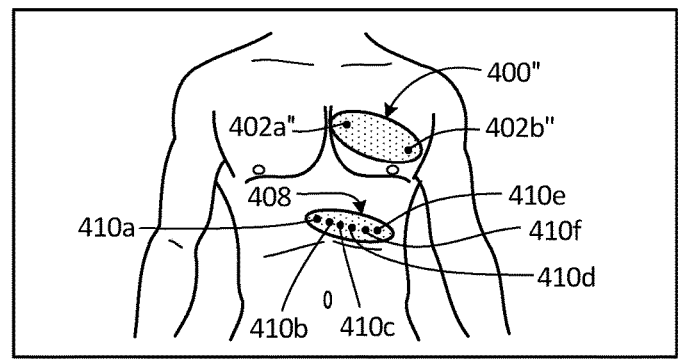

FIGS. 4a-4c are schematic views illustrating location of electrode placement according to an embodiment of the present invention. In at least embodiment, a minimum of two electrodes may be utilized to establish a single sensing vector determined based on the orientation of the electrodes relative to one another and to the patient. However, in other embodiments a plurality of electrodes may be utilized, wherein the placement of the electrodes relative to one another and to the patient provides additional sensing vectors. Because each sensing vector provides a different view of cardiac operation, utilizing a plurality of sensing vectors allows ischemic conditions to be detected in one of the vectors that might not be detectable in another vector. In one embodiment, an ischemic condition detected in one of the vectors results in an alert being generated and in ECG segments being provided to a remote monitoring center for review. In other embodiments, bimodal peaks detected in one sensing vector may be combined with PVC detections associated with a second, different sensing vector. Thus, detection of bimodal peaks and PVCs by different sensing vectors may be fused to detect potential ischemic conditions.

Figure 5:
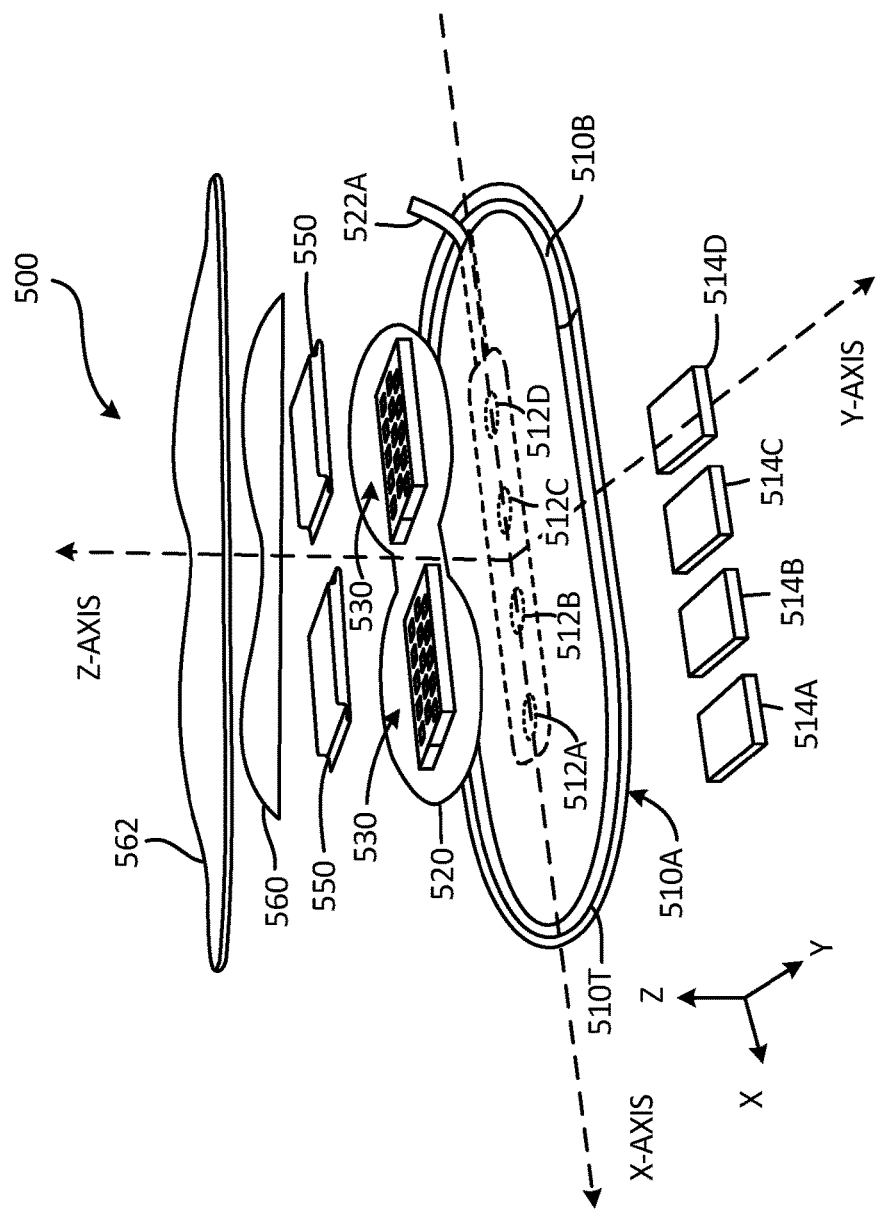
FIG. 5 is a schematic diagram of an adherent device for detecting electrocardiogram signals, according to one or more embodiments of the present invention.

In addition, as discussed in more detail with respect to FIG. 5, the utilization of a plurality of sensing vectors allows for localization estimates to be generated regarding the location of the potential ischemia. The localization estimate may be utilized to aid physicians/experts in verifying the detected ischemic condition. For example, if a particular cardiac region is identified as potentially ischemic, a HCP may utilize the location estimate to direct imaging of the patient's heart to confirm the diagnosis of ischemia.

In the embodiment shown in FIG. 4a, adherent patch 400 is affixed to the chest of patient P, and includes four electrodes labeled 402a, 402b, 402c, and 402d. Each pair of electrodes provides a sensing vector, such that utilization of four electrodes provides the potential to monitor six different sensing vectors. Sensing vectors include those created by the following pairs of electrodes (402a-402b), (402a-402c), (402a-402d), (402b-402c), (402b-402d), and (402c-402d). As discussed above, one or more of the sensing vectors may be utilized to detect potentially ischemic conditions. In addition, in other embodiments an ischemic condition detected by a particular sensing vector (or plurality of sensing vectors) can be utilized to generate a location estimate associated with the detected ischemic event.

In the embodiment shown in FIG. 4b, adherent patch 400' is utilized in conjunction with secondary medical device (e.g., adherent patch) 404. In this embodiment, adherent patch 400' includes two electrodes 400a and 400b, and secondary adherent patch 404 includes a single electrode 400c. In one embodiment, sensing circuitry utilized by adherent patch 400' is coupled to utilize electrode 400c in combination with electrodes 400a and 400b to generate one or more sensing vectors. In this embodiment, three sensing vectors may be selected from, including those generated by electrode pairs (400a, 400b), (400a, 400c), and (400b, 400c). A benefit of utilizing first adherent patch 400' in conjunction with second adherent patch 404 is the ability to select the sensing vector to be monitored via selective placement of second adherent patch 404. For example, if a doctor/physician would like to monitor a particular sensing vector corresponding with a particular view/location associated with the patient's heart, the physician can select the desired location for second adherent patch 404, and utilize the sensing vector created between electrodes on adherent patch 400' and electrodes included on secondary medical device 404.

In the embodiment shown in FIG. 4c, adherent patch 400" is utilized in conjunction with precordial adherent patch 408. In this embodiment, adherent patch 400" includes two electrodes 402a" and 402b", and precordial adherent patch 408 includes a plurality of electrodes 410a, 410b, 410c, 410d, 410e, and 410f (collectively, electrodes 410). In one embodiment, sensing circuitry utilized by adherent patch 400" is coupled to monitor sensing vectors created between electrodes located on adherent patch 400" and electrodes included on precordial adherent patch 408. The inclusion of a plurality of electrodes 410 generates a plurality of sensing vectors that may be analyzed. The location of precordial adherent patch 408 coupled with the large number of electrodes provides for more granular localization of potential ischemic conditions.

In one embodiment, localization of an ischemic condition is based on a look-up table, wherein each sensing vector is associated with a particular location of the patient's heart. Analysis of each of the plurality of sensing vectors is conducted—including analysis of high-frequency components and low-frequency components associated with each sensing vector. The sensing vector identified as most strongly indicating an ischemic condition (e.g., sensing vector with the highest count of bimodal detects/PVC beat detects) is selected, and the look-up table is utilized to estimate a location of the potential ischemia. In this embodiment, included in the generated alert indicating a potential ischemic event, the localized estimate of the detected ischemia is provided to the remote monitoring center for review. A benefit of this approach is that it provides the HCP with a particular area of the patient's heart for which additional tests, such as medical imaging, may be appropriate.

[Can we mock-up a lookup table for this embodiment?]

FIG. 5 is an exploded view, respectively, of monitoring device 500 with ischemia monitoring, according to one or more embodiments of the present disclosure. In the embodiment shown in FIG. 5, monitoring device 500 is an adherent device, but as described above may also be implemented as an implantable device, an injectable device, or similar wearable device. In the embodiment shown in FIG. 5, adherent device 500 includes adherent tape 510T, electrodes 512A, 512B, 512C, 512D with gels 514A, 514B, 514C, 514D, printed circuit board (PCB) 520, flexible connected 522A, electrical components/sensors 530 mounted on PCB 520, batteries 550, electronics housing cover 560, and flexible cover 562.

Adherent device 500 comprises at least two electrodes—although the embodiment shown in FIG. 5 includes electrodes 512A, 512B, 512C and 512D. Adherent device 500 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 500 comprises a first side, or a lower side 510A, that is oriented toward the skin of the patient when placed on the patient. The adherent patch 500 may also comprise a tape 510T which is a material, preferably breathable, with an adhesive (not shown) to adhere to patient P. Electrodes 512A, 512B, 512C and 512D are affixed to adherent patch 500. In many embodiments, at least four electrodes are attached to the patch. Gels 514A, 514B, 514C and 514D can each be positioned over electrodes 512A, 512B, 512C and 512D, respectively, to provide electrical conductivity between the electrodes and the skin of the patient. Adherent patch 500 also comprises a second side, or upper side 510B. In many embodiments, electrodes 512A, 512B, 512C and 512D extend from lower side 510A through adherent patch 500 to upper side 510B. An adhesive can be applied to upper side 510B to adhere structures, for example a breathable cover, to the patch such that the patch can support the electronics and other structures when the patch is adhered to the patient. In many embodiments, adherent patch 500 may comprise a layer of breathable tape 510T, for example a tricot-knit polyester fabric, to allow moisture vapor and air to circulate to and from the skin of the patient through the tape. Electrical signals received at electrodes 512A-512D may be communicated to electronic components 530 via flexible connection 522A, which is connected to a PCB (not shown). Cover 560 is positioned over batteries 550 and electronic components 530 to provide protection for both. In addition, flexible cover 562 is positioned to encase the flexible PCB 520, electronics components 530, and/or adherent patch 510 so as to protect at least the electronics components and the PCB.

In addition, electronic components 530 may include ECG circuitry utilized to generate electrocardiogram signals and data from two or more of electrodes 512A, 512B, 512C and 512D in many ways. In some embodiments, ECG circuitry (not shown) is connected to inner electrodes 512B and 512C, which may comprise sense electrodes of the impedance circuitry as described above. In many embodiments, the ECG circuitry may measure the ECG signal from electrodes 512A and 512D when current is not passed through electrodes 512A and 512D. In addition, electronic components 530 may include bioimpedance circuitry connected to two or more of electrodes 512A, 512B, 512C and 512D to allow electronic components 530 to measure a bioimpedance associated with the patient. In addition, electronic components 530 may include an accelerometer configured to measured motion of the patient. In other embodiments, ECG circuitry may utilize any combination of electrodes 512A, 512B, 512C, and 512D to sample various sensing vectors (e.g., 512A-512C, and 512B-512C).

In addition, electronic circuitry 530 may comprise a processor module that can be configured to analyze physiological parameters monitored by adherent device 500 and to control collection and transmission of data from the electrocardiogram circuitry. In one embodiment, the processor module included as part of electronic circuitry 630 comprises a tangible medium, for example read only memory (ROM), electrically erasable programmable read only memory (EEPROM) and/or random access memory (RAM). Tangible medium may, for example, store RAZ thresholds and PVC beat thresholds to be utilized in detecting ischemic conditions. Processing of monitored physiological parameters such as ECG signals may be distributed between the local processor module included as part of electronic circuitry 530 and remote monitoring system 106 (shown in FIG. 1).

In one embodiment, a processor and/or a processing module include electronic circuitry configured to filter and process monitored ECG signals of a patient, detect RAZ/bimodal morphologies within the HF QRS complexes, detect PVC beats within the low frequency components, and utilized the detected RAZ/bimodal morphologies and PVC detections to detect potential ischemic conditions. In some embodiments, this may further include determining/estimating the location of the ischemic condition. The detected ischemic condition, in combination with relevant ECG data is provide to remote monitoring center 106 for review/verification.

In many embodiments, electronics components 530 comprise wireless communications circuitry (not shown) to communicate with remote center 106. The PCB (not shown)

may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the electrocardiogram signal or other features collected by the adherent device 500. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection.

In this way, the present disclosure provides a system and method of extracting high-frequency components and low-frequency components from a monitored ECG signal. The high-frequency components are analyzed to detect a bimodal morphology, while the low-frequency components are analyzed to detect PVC beats. Detected bimodal morphology and PVC beat density/frequency are utilized to detect the potential for an ischemic event. In response, an alert is generated and relevant ECG segments are provided to a remote monitoring center for review/verification of the detected ischemia.

Discussion of Possible Embodiments

The following are non-exclusive descriptions of possible embodiments of the present invention.

In one embodiment, a method of detecting ischemia comprises sensing an electrocardiogram (ECG) signal and extracting high-frequency components and low-frequency components associated with the sensed ECG signal. Reduced amplitude zones (RAZs) are detected based on the extracted high-frequency components and premature ventricular contraction (PVC) beats are detected based on the extracted low-frequency component. Potential ischemic conditions are detected based on detection of both RAZs and PVC beats.

The method of the preceding paragraph can optionally include, additionally and/or alternatively any, one or more of the following features, configurations and/or additional components.

The method may further include wherein extracting high-frequency components includes extracting components in a frequency range of 150-250 Hertz (Hz).

The method may further include wherein extracting high-frequency components includes extracting high frequency components associated with QRS complex portions of the sensed ECG signal (HF QRS).

The method may further include identifying a HF QRS envelope associated with the HF QRS signal.

The method may further include wherein a RAZ counter is incremented for each RAZ detected, The method may further include wherein a PVC counter is incremented for each PVC beat detected.

The method may further include wherein potential ischemia is identified when both the PVC counter and the RAZ counter exceed threshold values.

The method may further include wherein detecting premature ventricular contraction (PVC) beats in the low-frequency components includes detecting density and/or frequency attributes associated with detected PVC beats.

According to another embodiment, a method of localizing detected ischemia comprises monitoring electrocardiogram (ECG) signals from a plurality of electrodes to generate a plurality of ECG sensing vectors and extracting high-frequency components associated with each of the plurality of ECG sensing vectors. Reduced amplitude zones (RAZs) are detected in the plurality of extracted high-frequency components and an ischemic condition is detected based on one or more of the extracted high-frequency components, wherein detection is based in part on the presence of detected RAZs in the extracted high-frequency components. A location estimate for the detected ischemic condition may then be generated based on the sensing vectors utilized to detect the RAZs.

The method of the preceding paragraph can optionally include, additionally and/or alternatively any, one or more of the following features, configurations and/or additional components.

The method may further include detecting premature ventricular contractions (PVCs) in one or more of the plurality of ECG sensing vectors.

The method may further include wherein detecting ischemia is further based on a frequency and/or density of detected PVCs in one or more of the plurality of ECG sensing vectors.

The method may further include wherein generating the location estimate for the detected ischemic condition is based on identification of the one or more sensing vectors in which bimodal peaks were detected.

The method may further include wherein generating the location estimate includes utilizing a look-up table that relates each of the plurality of sensing vectors to a particular cardiac location.

According to another embodiment, a system for monitoring electrocardiogram (ECG) signals and detecting potential ischemic conditions is comprised of a first medical device and a processing module. The first medical device includes one or more electrodes and sensing circuitry to monitor ECG signals associated with a patient. The processing module is configured to receive the monitored ECG, and includes filtering circuitry to extract high-frequency components and low-frequency components from the monitored ECG. The processing module analyzes the high frequency components to detect reduced amplitude zones (RAZs) and analyzes the low-frequency components to detect premature ventricular contractions (PVCs), wherein the processing module identifies potential ischemic conditions based on a combination of RAZs and PVCs.

The system of the preceding paragraph can optionally include, additionally and/or alternatively any, one or more of the following features, configurations and/or additional components.

For example, the system may include a second medical device having one or more electrodes, wherein sensing circuitry included on the first medical device is configured to utilize the one or more electrodes on the second monitoring device to monitor sensing vectors that utilize electrodes on both the first medical device and the second medical device.

The processing module may further analyze the high-frequency components and low-frequency components associated with each sensing vector and in response identify those sensing vectors indicative of an ischemic condition.

The processing module may further generate an ischemic location estimate based on those sensing vectors indicating an ischemic condition.

The processing module may determine a density and/or frequency of detected PVC beats, and utilizes the determined density and/or frequency to identify potential ischemic conditions.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of detecting ischemia, the method comprising:
   sensing an electrocardiogram (ECG) signal;
   extracting low-frequency components associated with the sensed ECG signal;
   detecting premature ventricular contraction (PVC) beats in the low-frequency components;
   incrementing a PVC counter in response to each detected PVC beat on a beat-by-beat basis;
   extracting high-frequency components associated with the sensed ECG signal, wherein extracting high-frequency components includes extracting high frequency components associated with QRS complex portions of the sensed ECG signal (HF QRS) and rejecting QRS complex portions associated with detected PVC beats;
   detecting a reduced amplitude zone (RAZ) in the HF QRS on a beat-by-beat basis;
   incrementing a counter in response to each detected RAZ; and
   identifying potential ischemia based on the PVC counter and the RAZ counter.

2. The method of claim 1, wherein extracting high-frequency components includes extracting components in a frequency range of 150-250 Hertz (Hz).

3. The method of claim 1, further including identifying a HF QRS envelope associated with the HF QRS signal.

4. The method of claim 1, wherein potential ischemia is identified when both the PVC counter and the RAZ counter exceed threshold values.

5. The method of claim 1, wherein detecting premature ventricular contraction (PVC) beats in the low-frequency components includes detecting density and/or frequency attributes associated with detected PVC beats.

6. The method of claim 1, wherein identifying potential ischemia based on detection of both RAZs and PVC beats comprises identifying based on an amount of RAZ beats and an amount of PVC beats.

7. The method of claim 1, wherein extracting low-frequency components includes extracting components in a frequency range of 0-40 Hertz (Hz).

* * * * *